United States Patent [19]

Boar et al.

[11] Patent Number: 5,747,515

[45] Date of Patent: May 5, 1998

[54] HETEROCYCLIC COMPOUNDS AND COMPOSITIONS HAVING NEVROPHARMACOLOGICAL POTENTIAL

[75] Inventors: Robin Bernad Boar, Herts; Alan John Cross, Surrey; Duncan Alastair Gray, Powys; Richard Alfred Green, Oxon, all of United Kingdom

[73] Assignee: Astra Aktiebolag, Sodertalje, Sweden

[21] Appl. No.: 379,467

[22] PCT Filed: Jul. 5, 1994

[86] PCT No.: PCT/SE94/00664

§ 371 Date: Jan. 30, 1995

§ 102(e) Date: Jan. 30, 1995

[87] PCT Pub. No.: WO95/01967

PCT Pub. Date: Jan. 19, 1995

[30] Foreign Application Priority Data

Jul. 6, 1993 [SE] Sweden ................... 9302333

[51] Int. Cl.$^6$ ................... A61K 31/415; A61K 31/42; C07D 263/32; C07D 277/24
[52] U.S. Cl. ................... 514/359; 514/370; 514/365; 514/377; 514/374; 548/233; 548/235; 548/193; 548/203; 548/100
[58] Field of Search ................... 548/233, 235, 548/236, 190, 194, 193, 200, 202, 203, 100, 331.5, 341.1, 343.1, 346.1; 514/374, 377, 370, 359, 398, 365

[56] References Cited

U.S. PATENT DOCUMENTS

| | | | |
|---|---|---|---|
| 4,544,664 | 10/1985 | Karjalainen et al. | 514/396 |
| 4,649,146 | 3/1987 | Takaya et al. | 514/307 |
| 4,960,900 | 10/1990 | Danree et al. | 548/203 |
| 5,340,815 | 8/1994 | Connor et al. | 514/269 |
| 5,356,898 | 10/1994 | Belliotti et al. | 514/269 |

FOREIGN PATENT DOCUMENTS

| | | |
|---|---|---|
| 0 477 141 | 3/1992 | European Pat. Off. . |
| 121520 | 6/1975 | Germany . |
| 2-91076 | 3/1990 | Japan . |
| 92/22537 | 12/1992 | WIPO . |

OTHER PUBLICATIONS

Walker et al., J. Het. Chem., 24, 1485–6, 1987.
Shafiee et al., J. Het. Chem., 26, 709–11, 1989.
Shafiee et al., J. Het. Chem., 23, 861–4, 1986.
LaMattina et al., Tet. Lett., 25(28), 2957–60.
Konig et al., Liebigs Ann. Chem., 668–82, 1981.
Ross et al., J. Med. Chem., 22(4), 412–17, 1979.
Caldwell et al., J. Chem. Soc. Perkin Trans. I, 2305–2310, 1987.
Kreutzberger et al., Archiv der Pharm. 314, 385–91, 1981.
Pascual, Helv. Chim. Acta, 74, 531–42, 1991.
Bolt et al., Biochem. Pharm., 23, 1963–8.
Ohler et al., Chem. Ber., 118, 4099–4130, 1985.
Meyers et al., J. Org. Chem., 47, 2999–3000, 1982.
Moriarty et al., Synthesis, 845–6, Sep. 1992.
Dondoni et al., "Synthesis of (Trimethylsilyl)thiazoles ...", J. Org. Chem. 1988, 53, 1748–1761.

Primary Examiner—Johann Richter
Assistant Examiner—Laura Cross Lutz
Attorney, Agent, or Firm—White & Case

[57] ABSTRACT

Novel heterocyclic compounds having a structure according to general formula (1), pharmaceutically acceptable acid addition salts and solvates thereof are described as having a pharmacological profile showing potential for treatment of acute and chronic neuropsychiatric disorders which are known as progressively deteriorating conditions leading to neuronal cell death and dysfunction. Pharmaceutical formulations are described as containing said therapeutic compounds.

7 Claims, No Drawings

5,747,515

HETEROCYCLIC COMPOUNDS AND COMPOSITIONS HAVING NEVROPHARMACOLOGICAL POTENTIAL

NEW COMPOUNDS

This is a 371 of PCT/SE94/00664 filed Jul. 5, 1994.

FIELD OF THE INVENTION

The present invention relates to novel heterocyclic compounds having therapeutic activity, processes and intermediates for their preparation, pharmaceutical formulations containing said compounds and the medicinal use of said compounds.

BACKGROUND OF THE INVENTION

There exists a large group of acute and chronic neuropsychiatric disorders for which safe and clinically effective treatments are not currently available. This diverse group of disorders encompasses a broad spectrum of initial events which are characterised by the initiation of progressive processes that sooner or later lead to neuronal cell death and dysfunction. Stroke, cerebral ischaemia, trauma or a neurodegenerative disease such as Alzheimer's disease or Parkinson's disease are all commonly occurring conditions that are associated with neurodegeneration of the brain and/or spinal cord.

The ongoing search for potential treatments of neurodegenerative disorders has involved investigation of excitatory amino acid antagonists, inhibitors of lipid peroxidation, calcium channel antagonists, inhibitors of specific pathways of the arachidonic acid cascade, kappa opioid agonists, adenosine agonists, PAF antagonists and diverse other agents. At the present time there is no consensus of the relative importance of the role played by compounds belonging to any of these general classes.

In a paper on the thermal and photochemical isomerisations of isoxazoles, A. Padwa et al (J. Amer. Chem. Soc., 1975, 97, 6484–6491) describe methylphenyl(2-phenyl-5-methyloxazol-4-yl) carbinol:

No pharmacological activity is ascribed to said compound.

In patent application EP 313 984, the bromo derivative:

is described as an intermediate for the synthesis of imidazole or triazole based antifungal agents.

In patent application WO 91/08744, 4-hydroxythiazole derivatives are claimed which are 5-lipoxygenase inhibitors. One example of such compounds is:

4-Oxygenated thiazoles are not included within the scope of the present invention.

In patent application EP 351 194 and in J. Med. Chem., 1991 34, 2176-2186, compounds of the general formula:

$$Ar^1-A-X-Ar^2-\underset{OR^2}{\overset{R^1}{\underset{|}{C}}}-Q$$

wherein Q is thiazolyl, $Ar^1$ is aryl of up to 10 carbon atoms, $Ar^2$ is 6-membered aryl, X is O, S, SO, $SO_2$ or NH and A is as direct link to X or is (1–6C)alkylene, (3–6C)alkenylene, (3–6C)alkynylene or cyclo(3–6C)alkylene are disclosed as 5-lipoxygenase inhibitors. The substituent $Ar^1$-A-X is not included within the scope of $R^1$ in claim 1 of the present invention.

In patent application EP 390 558, imidazoles of the following general structure:

are disclosed as aromatase inhibitors. Such compounds are deleted from the scope of the present invention by a disclaimer in claim 1.

In patent application EP 477 141, compounds of the general formula:

wherein Z is a five-membered aza-aromatic ring and X is cyano, carbamoyl or substituted carbamoyl are claimed. Said compounds are aromatase inhibitors. Specific examples are 1-(4-cyanophenyl)-1-(5-thiazolyl)ethene and 1-(4-cyanophenyl)-1-(5-thiazolyl)ethanol. Such substituents X are not included within the scope of the present invention.

In Tetrahedron, 1971, 27, 1211-1219 the compound 1-(1, 2-dimethyl-4-imidazolyl)-1-phenylethanol is described. This compound is deleted from the scope of the present invention by a disclaimer in claim 1.

THE PRESENT INVENTION

A primary objective of the present invention is to provide structurally novel heterocyclic compounds which by virtue of their pharmacological profile are expected to be of value in the treatment of acute and chronic neuropsychiatric disorders characterised by progressive processes that sooner or later lead to neuronal cell death and dysfunction. Such disorders include stroke; cerebral ischaemia; dysfunctions resulting from brain and/or spinal trauma; hypoxia and anoxia, such as from drowning, and including perinatal and neonatal hypoxic asphyxial brain damage; multi-infarct dementia; AIDS dementia; neurodegenerative diseases such as Alzheimer's disease, Parkinson's disease, Huntington's chorea, epilepsy, multiple sclerosis and amytrophic lateral sclerosis; brain dysfunction in connection with surgery involving extracorporeal circulation or in connection with brain surgery, including endarterectomy of the carotid arteries; and CNS dysfunctions as a result of exposure to neurotoxins or radiation. This utility is manifested, for example, by the ability of these compounds to inhibit delayed neuronal death in the gerbil bilateral occlusion model of ischaemia.

The present invention relates to a compound having the general formula (1)

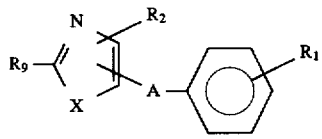
(1)

wherein:

X is O, S, Se or $NR_2$;

$R_1$ is one or more groups selected from H, lower alkyl, lower acyl, halogen, lower alkoxy, $CF_3$, OH, $NO_2$ or $NR_7R_8$ where $R_7$ and $R_8$ independently are H, lower alkyl or lower acyl;

$R_2$ is H, lower alkyl, lower alkoxy-lower alkyl, aryl-lower alkyl or $CF_3$; and when more than one $R_2$ groups are present these may be selected independently;

$R_9$ is H, lower alkyl, lower alkoxy-lower alkyl, aryl-lower alkyl, $CF_3$ or $NR_7R_8$;

and A is

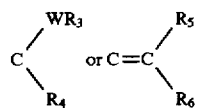

wherein

W is O, S, NH or N-lower alkyl, $R_3$ is H, lower alkyl or lower acyl, $R_4$ is lower alkyl, aryl-lower alkyl or $CF_3$;

$R_5$ and $R_6$ independently are H, lower alkyl, or aryl-lower alkyl;

with the proviso that when X is N-H or N-(aryl-methyl), then A is neither

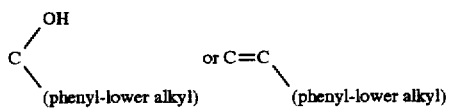

and with the proviso that the following compound is excluded:

1-(1,2-dimethyl-4-imidazolyl)-1-phenylethanol;

geometrical and optical isomers and racemates thereof where such isomers exist, as well as pharmaceutically acceptable acid addition salts thereof and solvates thereof.

The expression "pharmaceutically acceptable acid addition salts" is intended to include but is not limited to such salts as the hydrochloride, hydrobromide, hydroiodide, nitrate, hydrogen sulphate, dihydrogen phosphate, ethanedisulphonate, mesylate, fumarate, maleate and succinate.

Preferred embodiments of this invention relate to compounds having the general formula (2)

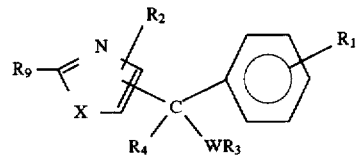
(2)

wherein:

X is O or S;

W is O;

and $R_1$, $R_2$, $R_3$, $R_4$ and $R_9$ are as previously defined above; and to compounds having the general formula (3)

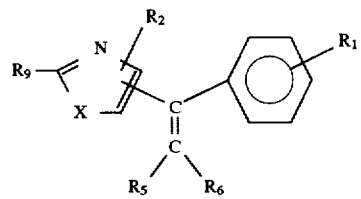
(3)

wherein:

X is O or S;

and $R_1$, $R_2$, $R_5$, $R_6$ and $R_9$ are as previously defined above.

Throughout the specification and the appended claims, a given chemical formula or name shall encompass all geometrical and optical isomers and racemates thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term "lower alkyl" denotes a straight or branched alkyl group having from 1 to 6 carbon atoms. Examples of said lower alkyl include methyl, ethyl, n-propyl, isopropyl, n-butyl, iso-butyl, t-butyl and straight- and branched-chain pentyl and hexyl.

Unless otherwise stated or indicated, the term "lower acyl" denotes a straight or branched acyl group having from 1 to 6 carbon atoms. Examples of said lower acyl include formyl, acetyl, propionyl, iso-butyryl, valeryl, and pivaloyl.

Unless otherwise stated or indicated, the term "lower alkoxy" denotes a straight or branched alkoxy group having from 1 to 6 carbon atoms. Examples of said lower alkoxy include methoxy, ethoxy, n-propoxy, iso-propoxy, n-butoxy, iso-butoxy, sec-butoxy, t-butoxy and straight-and branched-chain pentoxy and hexoxy.

Unless otherwise stated or indicated, the term "halogen" shall mean fluorine, chlorine, bromine or iodine.

Unless otherwise stated or indicated, the term "lower alkoxy-lower alkyl" denotes a lower alkyl group as defined above substituted by a lower alkoxy group as defined above. Examples of said lower alkoxy-lower alkyl include methoxymethyl, ethoxymethyl, methoxyethyl and ethoxyethyl.

Unless otherwise stated or indicated, the term "aryl" denotes a phenyl, naphthyl, furyl, thienyl, pyridyl or pyrrolyl group, itself optionally substituted.

Unless otherwise stated or indicated, the term "aryl-lower alkyl" denotes a lower alkyl group as defined above substituted by an aryl group as defined above. Examples of said aryl-lower alkyl include benzyl, phenethyl, phenylpropyl, 4-fluorophenylmethyl, furfuryl, 3-furylmethyl, tolylethyl and thienyl.

Among the most preferred compounds of formula (1) according to the present invention are:

1-(4-methyl-5-oxazolyl)-1-phenylethanol;

1-(4-methyl-5-thiazolyl)-1-phenylethanol;

1-(2-methoxyphenyl)-1-(4-methyl-5-oxazolyl)ethanol;

1-(4-methoxyphenyl)-1-(4-methyl-5-oxazolyl)ethanol;

1-(4-methyl-5-oxazolyl)-1-(2-trifluoromethyl-phenyl)-ethanol;

1-(4-methyl-5-thiazolyl)-1-phenylethene;

and pharmaceutically acceptable acid addition salts or solvates thereof.

The present invention also relates to processes for preparing the compound having formula (1). Throughout the following general description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups are described, for example, in "Protective Groups in organic Synthesis", T.W. Greene, Wiley-Interscience, New York, 1981.

Said compound wherein A is

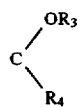

may be prepared by (a) reacting a compound of general formula (4) with an organometallic derivative of general formula (5)

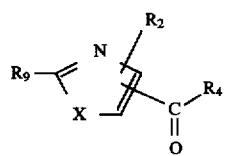 (4)

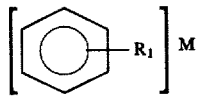 (5)

or (b) reacting a compound of general formula (6) with an organometallic derivative of general formula (7)

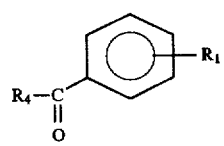 (6)

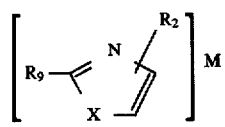 (7)

or (c) reacting a compound of general formula (8) with an organometallic derivative of general formula $R_4M$

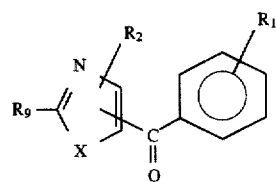 (8)

and quenching the reaction mixture with a proton source ($R_3$ is H) or an alkylating ($R_3$ is lower alkyl) or acylating ($R_3$ is lower acyl) reagent. Alternatively, the compound of formula (1)

wherein A is

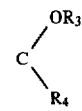

and $R_3$ is H may be first obtained as above and then converted into the compound wherein $R_3$ is lower alkyl or lower acyl.

The processes (a), (b) or (c) can be achieved for example, by reacting together a ketone of structure (4 or (6) or (8) with a preformed organometallic derivative (5) or (7) or $R_4M$ respectively in a suitable anhydrous solvent such as diethylether, tetrahydrofuran or hexane or mixtures thereof. Said reaction should be conducted at a suitable temperature, normally between $-100°$ C. and $+50°$ C. and preferably under an inert atmosphere, normally nitrogen or argon. In a specific variation, a solution of the ketone of structure (4) or (6) or (8) in anhydrous diethylether or tetrahydrofuran is added dropwise to the organometallic derivative (5) or (7) or $R_4M$ respectively in anhydrous diethylether or tetrahydrofuran or hexane or mixtures thereof at a temperature of about $-50°$ C. to $-78°$ C. and under an atmosphere of nitrogen. After a suitable period of time the reaction mixture is allowed to warm to room temperature and then quenched by the addition of water or a lower alcohol. The required product (1) wherein A is

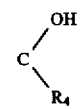

may then be isolated and purified and characterised using standard techniques.

Ketones of general formula (4) or (6) or (8) are either compounds which are commercially available or have been previously described in the literature, or compounds which can be prepared by the straightforward application of known methods.

Thus, the present invention also refers to some new intermediates of the general formulas (4) or (8), respectively, namely:

a compound of general formula (4)

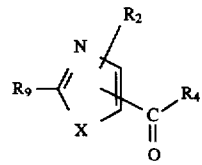 (4)

wherein

X is O, S or Se;

$R_4$ is $C_2$ to $C_6$ alkyl;

and $R_2$ and $R_9$ are as defined in claim 1 with the proviso that the following four compounds are excluded:
ethyl 4-thiazolyl ketone;
tert-butyl 5-thiazolyl ketone;
tert-butyl 5-oxazolyl ketone;
tert-butyl 4-tert-butyl-2-methyl-5-oxazolyl ketone;

or a compound of general formula (8)

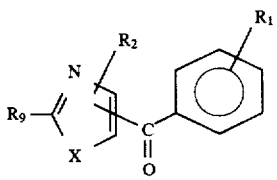

(B)

wherein X is O, S or Se; and $R_1$, $R_2$ and $R_9$ are as defined in claim 1, with the provisos that when $R_2$ and $R_9$ are both H, then $R_1$ is not H or 4-Br; and that when $R_9$ is H and $R_2$ is $CH_3$, then $R_1$ is not H or 4-OMe.

In the organometallic derivatives of general formula (5) or (7) or $R_4M$, M represents a metallic residue such as Li or Mg-halogen. Such compounds are either commercially available or have been previously described in the literature, or can be prepared by the straightforward application of known methods of organometallic chemistry.

Compounds of formula (1) wherein A is

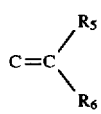

may be prepared by
(a) elimination of $HWR_3$ from a compound of formula (1) wherein A is

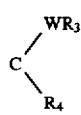

or (b) by using a compound of general formula (8) as the substrate for a standard alkene forming reaction such as the Wittig reaction, the Peterson reaction or the McMurry reaction.

The process (a) can be achieved, for example, by treatment of a solution of a compound of formula (1) wherein A is

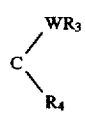

in a suitable inert solvent with an acid or a base or a reagent such as thionyl chloride or phosphorus oxychloride. Said reaction should be conducted at a suitable temperature, normally between −20° C. and the reflux temperature of the solvent. In a preferred variation, a solution of a compound of formula (1) wherein A is

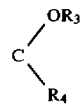

in a solvent such as dichloromethane or chloroform at 0° C. to 10° C. is treated with an acid such as anhydrous hydrogen chloride or p-toluenesulphonic acid, or with thionyl chloride. The reaction is then allowed to proceed at ambient temperature or above. The required product (1) wherein A is

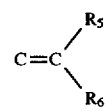

may then be isolated and purified and characterised using standard techniques.

Compounds of formula (1) wherein A is

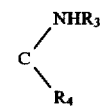

may be prepared by (a) using a compound of general formula (1) wherein A is

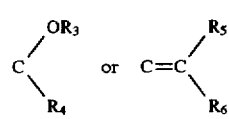

as the substrate for a Ritter reaction, or (b) by using a compound of general formula (1) wherein A is

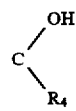

as the substrate for a Mitsunobu-type reaction.

Some compounds of general formula (1) contain an asymmetric centre and can thus exist in enantiomeric forms. These enantiomers may be separated using methods that will be well known to one skilled in the art. Such methods include, for example, (i) direct separation by means of chiral chromatography, for example, by HPLC using a chiral column;

or (ii) recrystallisation of the diastereomeric salts formed by reacting the base (1) with an optically active acid;

or (iii) derivatization of the compound of formula (1) by reaction with an optically active reagent, separation of the resultant diastereoisomeric derivatives by, for example, crystallisation or chromatography, followed by regeneration of the compound of formula (1).

Alternatively, compounds of formula (1) may be obtained directly in an optically active form by using a chemical or enzymatic based method of asymmetric synthesis.

Some compounds of general formula (1) wherein A is

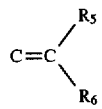

can exist as E and Z (trans and cis) isomers. Such isomers may be separated using standard techniques, for example, crystallisation or chromatography, that will be readily apparent to one skilled in the art.

PHARMACOLOGY

The neuroprotective properties of the compounds of formula (1) are exemplified by their ability to inhibit delayed neuronal death in the gerbil bilateral occlusion model of ischaemia.

Animals used were male Mongolian gerbils (60–80g). Drugs were dissolved in isotonic saline containing dimethylsulphoxide.

Ischaemia was induced in the gerbils by 5 minute occlusion of both carotid arteries following the procedure described by R. Gill, A.C. Foster and G.N. Woodruff, J. Neuroscience. 1987, 7, 3343-3349. Body temperature was maintained at 37° C. throughout. Restoration of blood flow after occlusion was checked visually and the animals were allowed to survive for 4 days. The extent of neuronal degeneration in the hippocampus was then assessed. The test compounds were administered (i.p.) as a single dose 60 minutes following occlusion. No administration was made prior to the occlusion. The effectiveness of the compounds of formula (1) in decreasing damage to the CA1/CA2 hippocampal neurones in gerbils following ischaemic insult clearly illustrates the usefulness of these compounds in preventing neurodegeneration. These compounds are therefore expected to be of value in the treatment of acute and chronic neuropsychiatric disorders characterised by progressive processes that sooner or later lead to neuronal cell death and dysfunction.

PHARMACEUTICAL FORMULATIONS

The administration in the novel method of treatment of this invention may conveniently be oral, rectal, topical or parenteral at a dosage level of, for example, about 0.01 to 1000 mg/kg, preferably about 1.0 to 500 mg/kg and especially about 5.0 to 200 mg/kg and may be administered on a regimen of 1 to 4 doses or treatments per day. The dose will depend on the route of administration, preferred routes being oral or intravenous administration. It will be appreciated that the severity of the disease, the age of the patient and other factors normally considered by the attending physician will influence the individual regimen and dosage most appropriate for a particular patient.

The pharmaceutical formulations comprising the compound of this invention may conveniently be tablets, pills, capsules, syrups, powders or granules for oral administration; sterile parenteral solutions or suspensions for parenteral administration; or as suppositories for rectal administration; or as suitable topical formulations. Conventional procedures for the selection and preparation of suitable pharmaceutical formulations are described, for example, in "Pharmaceuticals - The Science of Dosage Form Designs", M. E. Aulton, Churchill Livingstone, 1988.

To produce pharmaceutical formulations containing a compound according to the present invention in the form of dosage units for oral application the active substance may be admixed with an adjuvant/a carrier e.g. lactose, saccharose, sorbitol, mannitol, starches such as potato starch, corn starch or amylopectin, cellulose derivatives, a binder such as gelatine or polyvinyl-pyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compounds.

For the preparation of soft gelatine capsules, the active substance may be admixed with e.g. a vegetable oil or polyethylene glycol. Hard gelatine capsules may contain granules of the active substance using either the above mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.02% to about 20% by weight of the active substance herein described, the balance being sugar and mixture of ethanol, water, glycerol and propylene glycol. Optionally such liquid preparations may contain colouring agents, flavouring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may involve the use of surface acting agents to improve solubility. They may conventiently be provided in various dosage unit ampoules.

The necessary starting material for all Preparations and Examples were purchased commercially except as follows:

4-methyl-5-oxazolecarbonyl chloride (Indian J. Chem., Sect. B., 1985, 24B, 535-8);

5-acetyl-4-methyloxazole (Chem. Ber., 1960, 93, 1998-2001);

5-acetyl-4-methylthiazole (J. Agr. Food Chem., 1974, 22, 264-9);

5-acetyl-2,4-dimethyloxazole (Chem. Ber., 1960, 93, 1998-2001).

PREPARATION 1

N-Methoxy-N-methyl-4-methyl-5-oxazolecarboxamide

4-Methyl-5-oxazolecarbonyl chloride (15g) and N,O-dimethylhydroxylamine hydrochloride (11 g) in dry chloroform (looml) were cooled to OOC and dry pyridine (28.5g) was added. The mixture was allowed to warm to room temperature. After 30 minutes aqueous sodium hydrogen carbonate was added and the organic layer separated. The aqueous layer was extracted with dichloromethane. The combined organic layers were washed, dried and evaporated. The residue was purified by flash chromatography to yield the title compound as a white solid. M.p. 59®–60° C. $^1$H Nmr (CDC$_3$) 2.5, 3.34 and 3.82 (each 3H, s) and 7.86 (1H, S) ppm. Found: C, 49.0; H, 5.6; N, 16.4. C$_7$H$_{10}$N$_2$O$_3$ requires C, 49.4; H, 5.9; N, 16.5%

PREPARATION 2

4-Methyl-5-oxazolyl Phenyl Ketone

Phenyllithium (1.8M solution in cyclohexane-diethylether, 11.7ml) in dry tetrahydrofuran was stirred and cooled to –70° C. under an atmosphere of dry nitrogen and N-methoxy-N-methyl-4-methyl-5-oxazolecarboxamide (3.0g) in dry tetrahydrofuran was added dropwise. After 30 minutes the mixture was allowed to warm to room temperature. Ethanol (5ml) was added followed by saturated aqueous sodium chloride. The mixture was extracted with dichloromethane and the material thus obtained was purified by flash chromatography to give the title compound. M.p. 84–86° C. $^1$H Nmr (CDCl$_3$) 2.59 (3H, s), 7.5-7.68 (3H, m) and 7.96–8.06) (3H, m) ppm.

EXAMPLE 1

1-(4-Methyl-5-oxazolyl)-1-phenylethanol

5-Acetyl-4-methyloxazole (5g) in dry diethylether (25ml) at –70° C. under a nitrogen atmosphere was treated dropwise with phenyllithium (1.8M solution in cyclohexane-diethylether, 27ml). After 45 minutes the mixture was allowed to warm to room temperature and water (10 ml) was added. The mixture was poured into saturated aqueous sodium chloride and extracted with dichloromethane. The product thus obtained was crystallised from diethylether to give 1-(4-methyl-5-oxazolyl)-1-phenylethanol, m.p. 102–104° C.

$^1$H Nmr (CDC$_3$) 1.94 (3H, s), 2.0 (3H, s), 7.25-7.45 (5H, m) and 7.7 (1H, s) ppm.

$^{13}$C Nmr (CDC$_3$) 12.5, 29.7, 72.7, 125.1, 127.6, 128.4, 131.4, 145.2, 148.6 and 149.8 ppm.

Found: C, 70.9; H, 6.6; N, 6.5. C$_{12}$H$_{13}$NO$_2$ requires C, 70.9; H, 6.45; N, 6.9%

EXAMPLE 2

1-(4-Methyl-5-thiazolyl)-1-phenylethanol

4-Methylthiazole (log) in dry tetrahydrofuran (50ml) at –70° C. was stirred under a nitrogen atmosphere and n-butyllithium (2.5M solution in hexane, 44.4 ml) was added dropwise. After 30 minutes, trimethylsilylchloride (12.8 ml) was added and the reaction mixture was allowed to warm to room temperature. After 30 minutes the mixture was cooled to -70° C. and n-butyllithium (44.4ml) was added dropwise. After 30 minutes, acetophenone (12.9ml) was added dropwise and the mixture stirred at –70° C. for 1 hour. The reaction mixture was allowed to warm to room temperature and aqueous sodium hydrogen carbonate was added. The organic layer was separated and the aqueous layer was extracted with diethylether. The combined organic layers were then worked up to afford the title compound as a white solid, m.p. 128.5–129.5° C.

$^1$H Nmr (CDCl$_3$) 2.01 and 2.1 (each 3H, s), 3.06 (1H, br s), 7.24-7.47 (5H, m) and 8.5 (1H, s) ppm.

$^{13}$C Nmr (CDC$_3$) 16.2, 31.9, 73.7, 125.5, 127.6, 128.4, 139.7, 145.9, 148.8 and 148.9 ppm.

Found: C, 65.6; H, 5.9; N, 6.3. C$_{12}$H$_{13}$NOS requires C, 65.7; H, 6.0; N, 6.4%

Identical material was also obtained by the reaction of 5-acetyl-4-methylthiazole with phenyllithium according to the general method of Example 1.

EXAMPLE 3

1-(2-Methoxyphenyl)-1-(4-methyl-5-oxazolyl)ethanol

2-Bromoanisole (4.86g) in anhydrous diethylether (10 ml) was added dropwise to a stirred solution of n-butyllithium (2.5M solution in hexane, 10.4 ml) in diethylether (30 ml) at –70° C. under an atmosphere of dry nitrogen. After 45 minutes, 5-acetyl-4-methyloxazole (2.5g) in diethylether (loml) was added dropwise. After a further 1 hour at –70° C. the reaction mixture was allowed to warm to room temperature and was stirred overnight. Saturated aqueous sodium hydrogen carbonate was added. The organic layer was separated and the aqueous layer was extracted with diethylether. The combined organic layers were further processed to give the title compound as a white solid, m.p. 74–75° C.

$^1$H Nmr (CDCl$_3$) 1.92, 2.0 and 3.78 (each 3H, s), 4.61 (1H, s), 6.92 (1H, d), 7.0 (1H, t), 7.26-7.37 (2H, m) and 7.64 (1H, s) ppm.

$^{13}$C Nmr (CDC$_3$) 12.1, 27.0, 55.6, 72.3, 111.5, 121.1, 126.6, 129.3, 130.2, 132.4, 148.0, 149.8 and 156.9 ppm.

Found: C, 66.8; H, 6.7; N, 6.05. C$_{13}$H$_{15}$NO$_3$ requires C, 66.9; H, 6.5; N, 6.0%

EXAMPLE 4

1-(4-Methoxvphenyl)-1-(4-methyl-5-oxazolyl)ethanol

Following the general method of Example 3 but starting with 4-bromoanisole, the title compound was prepared.

M.p. 115–116° C.

$^1$H Nmr (CDC$_3$) 1.9, 1.98 and 3.8 (each 3H, s), 3.07 (1H, s), 6.87 (1H, d), 7.33 (1H, d) and 7.65 (1H, s) ppm.

$^{13}$C Nmr (CDCl$_3$) 12.4, 29.7, 55.2, 72.3, 113.7, 126.4, 131.1, 137.5, 148.5, 150.0 and 159.0 ppm.

Found: C, 67.1; H, 6.5; N, 6.1. C$_{13}$H$_{15}$NO$_3$ requires C, 66.9; H, 6.5; N, 6.0%

EXAMPLE 5

1-(4-Methyl-5-oxazolyl)-1-(2-trifluoromethylphenyl)-ethanol

Following the general method of Example 3 but starting with 2-trifluoromethylbromobenzene, the title compound was prepared.

M.p. 108–109° C.

$^1$H Nmr (CDC$_3$) 1.95 and 2.02 (each 3H, s), 2.59 (1H, s), 7.43 and 7.56 (each 1H, t), 7.7 (1H, s) and 7.73–7.78 (2H, m) ppm.

Found: C, 57.3; H, 4.3; N, 5.1. C$_{13}$H$_{12}$F$_3$NO$_2$ requires C, 57.6; H, 4.5; N, 5.2%

Treatment of the above product with anhydrous hydrogen chloride in diethylether gave 1-(4-methyl-5-oxazolyl)-1-(2-trifluoromethylphenyl) ethanol hydrochloride as a white solid, m.p. 104–105° C.

Found: C, 50.6; H, 4.1; N, 4.5. C$_{13}$H$_{12}$F$_3$NO$_2$·HCl requires C, 50.7; H, 4.3; N, 4.55%

EXAMPLE 6

1-(4-Methyl-5-thiazolyl)-1-phenylethene 1-(4-Methyl-5-thiazolyl)-1-phenylethanol (2.5g) in chloroform (25ml) was treated with thionyl chloride (4.5ml).

The mixture was heated under reflux overnight and then evaporated to dryness. Aqueous sodium hydrogen carbonate was added and the mixture was extracted with dichloromethane. The material thus obtained was purified by flash chromatography to give the title compound as an oil. Treatment with anhydrous hydrogen chloride in diethylether gave 1-(4-methyl-5-thiazolyl) -1-phenylethene hydrochloride. m.p. 131–133.5° C.

1H Nmr ($d_6$-DMSO) 1.85 (3H, s), 5.15 and 5.52 (each 1H, s), 6.96-7.07 (5H, m) and 8.82 (1H, s) ppm.

$^{13}$C Nmr ($d_6$-DMSO) 15.4, 119.2, 126.6, 128.3, 128.5, 131.2, 138.8, 139.4, 148.7 and 152.4 ppm.

Found: C, 60.6; H, 5.0; N, 5.7. $C_{12}H_{11}NS \cdot HCl$ requires C, 60.6; H, 5.1; N, 5.9%

EXAMPLE 7

1- (4-Methyl) -5-oxazolyl) -1- (4-trifluoromethylphenyl)-ethanol

Following the general method of Example 3 but starting with 4-trifluoromethylbromobenzene, the title compound was prepared.

M.p. 89–91° C.

$^1$H Nmr ($CDCl_3$) 1.93 and 2.01 (each 3H, s), 3.18 (1H, s), 7.54 and 7.62 (each 2H, d) amd 7.7 (1H, s) ppm.

The corresponding hydrochloride salt was prepared, m.p. 110–111° C.

EXAMPLE 8

1-(4-Methoxyphenyl)-1-(2,4-dimethyl-5-thiazolvl)ethanol

Following the general method of Example 3 but starting with 4-bromoanisole and 5-acetyl-2,4-dimethylthiazole, the title compound was prepared. M.p. 114–115.5° C.

$^{13}$C Nmr ($CDC_3$) 16.2, 18.8, 31.9, 55.2, 73.5, 113.6, 126.8, 138.5, 139.2, 147.6, 159.2 and 162.3 ppm.

EXAMPLE 9

1-(4-Methyl-5-thiazolyl) -1-phenyl-2,2,2-trifluoroethanol

Following the general method of Example 2 but starting with 2,2,2-trifluoroacetophenone, the title compound was prepared.

M.p. 180–181.5° C.

$^1$H Nmr ($d_6$-DMSO) 1.6 (3H, s), 7.1 (5H, m) and 8.66 (1H, s) ppm.

EXAMPLE 10

1-(4-Methoxyphenyl)-1-(2,4-dimethyl-5-thiazolyl)ethene 1- (4-Methoxyphenyl) -1- (2, 4-dimethyl-5-thiazolyl) ethanol (3.69g) in chloroform (50ml) was treated with hydrogen chloride in dry diethyl ether (1M, 14.5ml). After 2 hours at room temperature, aqueous sodium hydrogen carbonate was added and the mixture was extracted with chloroform. The material thus obtained was purified by flash chromatography to yield the title compound.

$^1$H Nmr ($CDCl_3$) 2.2, 2.65 and 3.83 (each 3H, s), 5.27 and 5.60 (each 1H, s), and 6.86 and 7.28 (each 2H, d) ppm.

Hydrochloride, m.p. 139–140° C. $^{13}$C Nmr ($d_6$-DMSO) 15.1, 17.9, 55.1, 113.9, 117.1, 128.0, 131.0, 131.7, 138.0, 146.5, 159.4 and 164.3 ppm.

EXAMPLE 11

1-(2,4-Dimethyl-5-thiazolyl)-1-phenylethanol

The title compound was prepared following the general method of Example 1 but starting with 5-acetyl-2,4-dimethylthiazole.

M.p. 131–132° C. $^{13}$C Nmr ($CDC_3$) 16.2, 18.7, 32.3, 73.6, 125.4, 127.4, 128.3, 138.8, 146.4, 147.6 and 161.8 ppm.

EXAMPLE 12

1-(2,4-Dimethyl-5-oxazolyl)-1-phenylethanol

The title compound was prepared following the general method of Example 1 but starting with 5-acetyl-2,4-dimethyloxazole.

M.p. 94.5–96° C. $^{13}$C Nmr ($CDCl_3$) 12.3, 13.6, 29.8, 72.5, 125.1, 127.4, 128.2, 131.4, 145.6, 149.2 and 158.9 ppm.

EXAMPLE 13

1-Phenyl-1-(5-thiazolyl)ethanol n-Butyllithium (2.5M solution in hexane, 7ml) in diethyl ether (30ml) was stirred at −70° C. under a nitrogen atmosphere and 2-trimethylsilylthiazole (2.5g) in diethyl ether (10 ml) was added dropwise. After 30 minutes, acetophenone (2.3g) in diethyl ether (10 ml) was added dropwise. After a further 45 minutes the mixture was allowed to warm to room temperature and was then left overnight. Water was added and the mixture was extracted with diethyl ether. The material thus obtained was purified by flash chromatography to give the title compound.

M.p. 86–87° C. $^{13}$C Nmr ($CDCl_3$) 32.2, 73.3, 125.1, 127.5, 128.3, 139.4, 146.5, 148.6 and 153.1 ppm.

We claim:

1. A compound having the general formula (1)

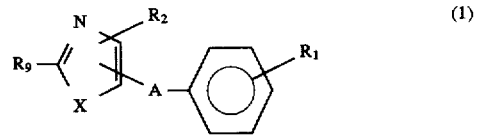

(1)

wherein:

X is O, S, or Se;

$R_1$ is one or more groups selected from H, lower alkyl, lower acyl, halogen, lower alkoxy, $CF_3$, OH, $NO_2$ or $NR_7R_8$ where $R_7$ and $R_8$ independently are H, lower alkyl or lower acyl;

$R_2$ is H, lower alkyl, lower alkoxy-lower alkyl, aryl-lower alkyl or $CF_3$;

$R_9$ is H, lower alkyl, lower alkoxy-lower alkyl, aryl-lower alkyl, $CF_3$ or $NR_7R_8$; and A is

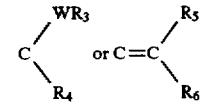

wherein

W is O, S, NH or N-lower alkyl;

$R_3$ is H, lower alkyl or lower acyl;

$R_4$ is lower aklyl, aryl-lower alkyl or lower perfluoroalkyl;

$R_5$ and $R_6$ independently are H, lower alkyl, or aryl-lower alkyl;

geometric and optical isomers and racemates thereof where such isomers exist, as well as pharmaceutically acceptable acid addition salts thereof and solvates thereof.

2. A compound according to claim 1 having the general formula (2)

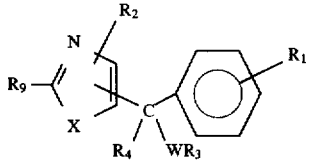
(2)

wherein:

X is O or S;

W is O and $R_1$, $R_2$, $R_3$, $R_4$ and $R_9$ are as defined in claim 1.

3. A compound according to claim 1 having the general formula (3)

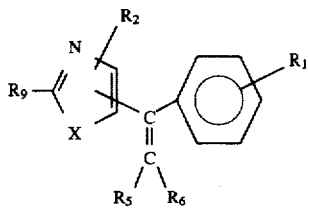
(3)

wherein:

X is O or S;

and $R_1$, $R_2$, $R_5$, $R_6$ and $R_9$ are as defined in claim 1.

4. A compound according to claim 1 selected from the group consisting of 1-(4-methyl-5-oxazolyl)-1-phenylethanol;

1-(4-methyl-5-thiazolyl)-1-phenylethanol;

1-(2-methoxyphenyl)-1-(4-methyl-5-oxazolyl)ethanol;

1-(4-methoxyphenyl)-1-(4-methyl-5-oxazolyl)ethanol;

1- (4-methyl-5-oxazolyl) -1- (2-trifluoromethyl-phenyl) -ethanol;

1-(4-methyl-5-thiazolyl)-1-phenylethene;

and pharmaceutically acceptable acid addition salts or solvates thereof.

5. A pharmaceutical formulation containing a compound having the general formula (1)

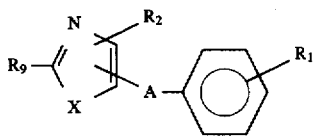
(1)

wherein:

X is O, S, or Se.;

$R_1$ is one or more groups selected from H, lower alkyl, lower acyl, halogen, lower alkoxy, $CF_3$, OH, $NO_2$ or $NR_7R_8$ where $R_7$ and $R_8$ independently are H, lower alkyl or lower acyl;

$R_2$ is H, lower alkyl, lower alkoxy-lower alkyl, aryl-lower alkyl or $CF_3$ and when more than one $R_2$ groups are present these may be selected independently;

$R_9$ is H, lower alkyl, lower alkoxy-lower alkyl, aryl-lower alkyl, $CF_3$ or $NR_7R_8$;

and A is

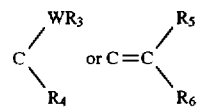

wherein

W is O, S, NH or N-lower alkyl;

$R_3$ is H, lower alkyl or lower acyl;

$R_4$ is lower alkyl, aryl-lower alkyl or $CF_3$;

$R_5$ and $R_6$ independently are H, lower alkyl, or aryl-lower alkyl;

geometric and optical isomers and racemates thereof where such isomers exist, as well as pharmaceutically acceptable acid addition salts thereof and solvates thereof, as active ingredient and a pharmaceutically acceptable carrier.

6. A compound as defined in claim 1 for the treatment of stroke; cerebral ischaemia; dysfunctions resulting from brain and/or spinal trauma; hypoxia and anoxia; multi-infarct dementia; AIDS dementia; neurodegenerative diseases; brain dysfunction in connection with surgery; and CNS dysfunctions as a result of exposure to neurotoxins or radiation.

7. A method for the treatment of acute and chronic neuropsychiatric disorders characterised by progressive processes that lead to neuronal cell death and dysfunction comprising administering to a host in need of such treatment a sufficient amount of a compound having the formula (1)

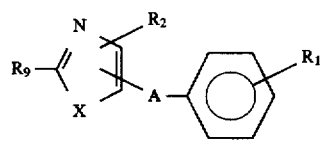
(1)

wherein:

X is O, S, Se, or NR2;

$R_1$ is one or more groups selected from H, lower alkyl, lower acyl, halogen, lower alkoxy, $CF_3$, OH, $NO_2$ or $NR_7R_8$ where $R_7$ and $R_8$ independently are H, lower alkyl or lower acyl;

$R_2$ is H, lower alkyl, lower alkoxy-lower alkyl, aryl-lower alkyl or $CF_3$ and when more than one $R_2$ groups are present these may be selected independently;

$R_9$ is H, lower alkyl, lower alkoxy-lower alkyl, aryl-lower alkyl, $CF_3$ or $NR_7R_8$;

and A is

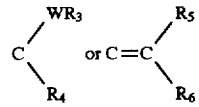

wherein

W is O, S, NH or N-lower alkyl;

$R_3$ is H, lower alkyl or lower acyl;

$R_4$ is lower alkyl, aryl-lower alkyl or $CF_3$;

$R_5$ and $R_6$ independently are H, lower alkyl, or aryl-lower alkyl;

with the proviso that when X is N-H or N-(aryl-methyl), then A is neither

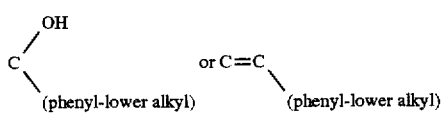
geometric and optical isomers and racemates thereof where such isomers exist, as well as pharmaceutically acceptable acid addition salts thereof and solvates thereof.
* * * * *